United States Patent
Kaib et al.

(10) Patent No.: US 11,198,017 B2
(45) Date of Patent: Dec. 14, 2021

(54) REMOTE MEDICAL DEVICE ALARM

(71) Applicant: ZOLL Medical Corporation, Chelmsford, MA (US)

(72) Inventors: Thomas E Kaib, Irwin, PA (US); Shane S Volpe, Saltsburg, PA (US); Richard A Rattanni, Verona, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 16/953,439

(22) Filed: Nov. 20, 2020

(65) Prior Publication Data
US 2021/0077820 A1 Mar. 18, 2021

Related U.S. Application Data

(63) Continuation of application No. 16/665,090, filed on Oct. 28, 2019, now Pat. No. 10,881,871, which is a (Continued)

(51) Int. Cl.
*A61N 1/39* (2006.01)
*G08B 3/10* (2006.01)
(Continued)

(52) U.S. Cl.
CPC .......... *A61N 1/3993* (2013.01); *A61B 5/0022* (2013.01); *A61B 5/01* (2013.01); (Continued)

(58) Field of Classification Search
CPC .................................................... A61N 1/3993
See application file for complete search history.

(56) References Cited

U.S. PATENT DOCUMENTS

| 4,094,310 A | 6/1978 | McEachern et al. |
| 4,632,122 A | 12/1986 | Johansson et al. |

(Continued)

FOREIGN PATENT DOCUMENTS

| CN | 201481410 U | 5/2010 |
| DE | 2644236 | 4/1978 |

(Continued)

OTHER PUBLICATIONS

European Patent Office, Office Action for Patent Application 11782349.2, dated May 27, 2020, 5 pages.
(Continued)

*Primary Examiner* — Travis R Hunnings
(74) *Attorney, Agent, or Firm* — Finch & Maloney PLLC

(57) ABSTRACT

A remote alarm for use with a wearable medical device. The remote alarm is configured to receive alarms, voice messages and prompts issued by the wearable medical device and to repeat those alarms, voice messages and prompts in a manner that can more easily be perceived by a patient wearing the wearable medical device or a bystander. The remote alarm can be configured to receive a communication from the wearable medical device, and in response, to identify one or more messages to be provided to the patient or a bystander. The messages may be provided audibly, visually, tactilely or combinations thereof. The remote alarm may further be configured to take certain actions depending upon the content of the communication, such as sending a telephone message to alert emergency personnel to the identity, location and medical condition of the patient, or sending an email.

20 Claims, 4 Drawing Sheets

Related U.S. Application Data continuation of application No. 16/185,123, filed on Nov. 9, 2018, now Pat. No. 10,485,982, which is a continuation of application No. 15/840,014, filed on Dec. 13, 2017, now Pat. No. 10,159,849, which is a continuation of application No. 14/579,615, filed on Dec. 22, 2014, now Pat. No. 9,925,387, which is a continuation of application No. 13/286,533, filed on Nov. 1, 2011, now Pat. No. 9,937,355.

(60) Provisional application No. 61/411,189, filed on Nov. 8, 2010.

(51) Int. Cl.
  *G08B 21/02* (2006.01)
  *G08B 25/01* (2006.01)
  *G08B 25/10* (2006.01)
  *A61B 5/00* (2006.01)
  *A61B 5/01* (2006.01)
  *A61B 5/024* (2006.01)
  *A61B 5/145* (2006.01)

(52) U.S. Cl.
  CPC ...... *A61B 5/02438* (2013.01); *A61B 5/14542* (2013.01); *A61B 5/742* (2013.01); *A61B 5/7405* (2013.01); *A61B 5/7455* (2013.01); *G08B 3/10* (2013.01); *G08B 21/02* (2013.01); *G08B 21/0277* (2013.01); *G08B 25/016* (2013.01); *G08B 25/10* (2013.01)

(56) References Cited

U.S. PATENT DOCUMENTS

| | | | |
|---|---|---|---|
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,153,584 A * | 10/1992 | Engira | A61B 5/0006 |
| | | | 128/903 |
| 5,228,449 A | 7/1993 | Christ et al. | |
| 5,348,008 A | 9/1994 | Bornn et al. | |
| 5,365,932 A | 11/1994 | Greenhut | |
| 5,652,570 A | 7/1997 | Lepkofker | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olsen et al. | |
| 5,929,601 A | 7/1999 | Kaib et al. | |
| 5,944,669 A | 8/1999 | Kaib | |
| 6,016,445 A | 1/2000 | Baura | |
| 6,065,154 A | 5/2000 | Hulings et al. | |
| 6,097,987 A | 8/2000 | Milani | |
| 6,169,397 B1 | 1/2001 | Steinbach et al. | |
| 6,221,010 B1 | 4/2001 | Lucas | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,405,082 B1 | 6/2002 | Borgenicht | |
| 6,406,426 B1 | 6/2002 | Reuss et al. | |
| 6,602,191 B2 | 8/2003 | Quy | |
| 6,609,023 B1 | 8/2003 | Fischell et al. | |
| 6,681,003 B2 | 1/2004 | Linder et al. | |
| 6,690,969 B2 | 2/2004 | Bystrom et al. | |
| 6,736,759 B1 | 5/2004 | Stubbs et al. | |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,980,112 B2 * | 12/2005 | Nee | A61N 1/37282 |
| | | | 340/539.12 |
| 6,990,373 B2 | 1/2006 | Jayne et al. | |
| 7,088,233 B2 | 8/2006 | Menard | |
| 7,149,579 B1 | 12/2006 | Koh et al. | |
| 7,220,235 B2 | 5/2007 | Geheb et al. | |
| 7,269,629 B2 | 9/2007 | Zmudzinski et al. | |
| 7,307,509 B2 | 12/2007 | Chriss | |
| 7,310,553 B2 | 12/2007 | Freeman | |
| 7,340,296 B2 | 3/2008 | Stahmann et al. | |
| 7,427,921 B2 | 9/2008 | Van Woudenberg | |
| 7,453,354 B2 | 11/2008 | Reiter et al. | |
| 7,488,293 B2 | 2/2009 | Marcovecchio et al. | |
| 7,794,384 B2 | 9/2010 | Sugiura et al. | |
| 7,831,303 B2 | 11/2010 | Rueter et al. | |
| 7,974,689 B2 | 7/2011 | Volpe et al. | |
| 7,991,460 B2 * | 8/2011 | Fischell | A61B 5/352 |
| | | | 600/519 |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 8,290,574 B2 | 10/2012 | Feild et al. | |
| 8,364,221 B2 | 1/2013 | Mannheimer et al. | |
| 8,369,944 B2 | 2/2013 | Macho et al. | |
| 8,428,704 B2 | 4/2013 | Johnson et al. | |
| 9,060,683 B2 | 6/2015 | Tran | |
| 9,427,564 B2 | 8/2016 | Kaib et al. | |
| 9,925,387 B2 | 3/2018 | Kaib et al. | |
| 9,937,355 B2 | 4/2018 | Kaib et al. | |
| 2003/0004547 A1 | 1/2003 | Owen et al. | |
| 2003/0095648 A1 | 5/2003 | Kaib et al. | |
| 2003/0128121 A1 * | 7/2003 | Nee | G08B 21/0453 |
| | | | 340/573.1 |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2004/0128310 A1 * | 7/2004 | Zmudzinski | H04W 68/00 |
| 2004/0204743 A1 | 10/2004 | McGrath et al. | |
| 2005/0038345 A1 | 2/2005 | Gorgenberg et al. | |
| 2005/0049515 A1 | 3/2005 | Misczynski et al. | |
| 2005/0131465 A1 | 6/2005 | Freeman et al. | |
| 2005/0177051 A1 * | 8/2005 | Almen | A61B 5/02405 |
| | | | 600/509 |
| 2005/0246199 A1 | 11/2005 | Futch | |
| 2005/0261598 A1 | 11/2005 | Banet et al. | |
| 2006/0036292 A1 | 2/2006 | Smith et al. | |
| 2006/0085049 A1 | 4/2006 | Cory et al. | |
| 2006/0136004 A1 | 6/2006 | Cowan et al. | |
| 2006/0160522 A1 | 7/2006 | Jennings | |
| 2006/0178706 A1 | 8/2006 | Lisogurski et al. | |
| 2006/0270952 A1 | 11/2006 | Freeman et al. | |
| 2007/0118056 A1 | 5/2007 | Wang et al. | |
| 2007/0161913 A1 | 7/2007 | Farrell et al. | |
| 2007/0169364 A1 | 7/2007 | Townsend et al. | |
| 2007/0239214 A1 | 10/2007 | Cinbis | |
| 2007/0239220 A1 | 10/2007 | Greenhut et al. | |
| 2007/0265671 A1 | 11/2007 | Roberts et al. | |
| 2008/0004536 A1 | 1/2008 | Baxi et al. | |
| 2008/0004904 A1 * | 1/2008 | Tran | A61B 8/565 |
| | | | 705/2 |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0058884 A1 | 3/2008 | Matos | |
| 2008/0103402 A1 | 5/2008 | Stickney et al. | |
| 2008/0177341 A1 | 7/2008 | Bowers | |
| 2008/0249591 A1 | 10/2008 | Gaw et al. | |
| 2008/0287749 A1 | 11/2008 | Reuter | |
| 2008/0294019 A1 | 11/2008 | Tran | |
| 2008/0306560 A1 * | 12/2008 | Macho | A61N 1/3993 |
| | | | 607/5 |
| 2008/0306562 A1 * | 12/2008 | Donnelly | A61N 1/0484 |
| | | | 607/6 |
| 2009/0005827 A1 | 1/2009 | Weintraub et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |

(56) References Cited

U.S. PATENT DOCUMENTS

| | | |
|---|---|---|
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082682 A1 | 3/2009 | Fischell et al. |
| 2009/0093687 A1 | 4/2009 | Telfort et al. |
| 2009/0096417 A1 | 4/2009 | Idzik et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2009/0307266 A1 | 12/2009 | Fleizach et al. |
| 2009/0318779 A1 | 12/2009 | Tran |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0102832 A1 | 4/2010 | Bartling et al. |
| 2010/0114206 A1 | 5/2010 | Kaemmerer et al. |
| 2010/0114243 A1 | 5/2010 | Nowak et al. |
| 2010/0198094 A1 | 8/2010 | Turicchia et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2011/0022105 A9 | 1/2011 | Owen et al. |
| 2011/0054264 A1 | 3/2011 | Fischell et al. |
| 2011/0080294 A1 | 4/2011 | Tanishima et al. |
| 2011/0093840 A1 | 4/2011 | Pynenburg et al. |
| 2011/0098765 A1 | 4/2011 | Patel |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0053479 A1 | 3/2012 | Hopenfeld |
| 2012/0146797 A1 | 6/2012 | Oskin et al. |
| 2012/0165684 A1 | 6/2012 | Sholder |

FOREIGN PATENT DOCUMENTS

| | | |
|---|---|---|
| EP | 0295497 | 9/1993 |
| EP | 0335356 | 3/1996 |
| EP | 1720446 | 2/2005 |
| EP | 1642616 | 4/2006 |
| EP | 1455640 | 1/2008 |
| JP | 5115450 | 5/1993 |
| JP | 20020922772 | 3/2002 |
| JP | 2002514107 | 5/2002 |
| JP | 2003260145 | 9/2003 |
| JP | 2008513112 | 5/2008 |
| JP | 2008302225 | 12/2008 |
| JP | 2008302228 | 12/2008 |
| JP | 2009510631 | 3/2009 |
| JP | 2009521260 | 6/2009 |
| WO | 19970000708 | 1/1997 |
| WO | 200002484 | 1/2000 |
| WO | 2004054656 | 7/2004 |
| WO | 2004067083 | 8/2004 |
| WO | 2005082454 | 9/2005 |
| WO | 20060033812 | 3/2006 |
| WO | 2006050235 | 5/2006 |
| WO | 2007019325 | 2/2007 |
| WO | 20070041329 | 4/2007 |
| WO | 20070073455 | 6/2007 |
| WO | 2007077997 | 7/2007 |
| WO | 2009034506 | 3/2009 |
| WO | 2010025432 | 3/2010 |

OTHER PUBLICATIONS

Japan Patent Office, Office Action for Patent Application 2018-232642 with English machine translation, dated Nov. 19, 2019, 10 pages.

American Journal of Respiratory and Critical Care Medicine, vol. 166, pp. 111-117 (2002), American Thoracic Society, ATS Statement: Guidelines for the Six-Minute Walk Test, available at hht://ajrccm.atsjournals.org/cgi/content/full/166/1/111.

DeBock, et al., "Captopril treatment of chronic heart failure in the very old," J. Gerontol. (1994) 49: M148-M152.

International Search Report and Written Opinion from corresponding International Application No. PCT/US2011/059345, dated Jan. 25, 2012.

O'Keeffe et al., "Reproducability and responsiveness of quality of life assessment and six minute walk test in elderly heart failure patients," Heart (1998) 80: 377-382.

Office Action received in Japan Patent Application 2020-166858, dated Sep. 7, 2021, 12 pages.

* cited by examiner

REMOTE MEDICAL DEVICE ALARM

CROSS-REFERENCE TO RELATED APPLICATIONS

This application is a continuation of U.S. patent application Ser. No. 16/665,090 (filed 28 Oct. 2019), which is a continuation of U.S. patent application Ser. No. 16/185,123 (filed 9 Nov. 2018, now U.S. Pat. No. 10,485,982), which is a continuation of U.S. patent application Ser. No. 15/840,014 (filed 13 Dec. 2017, now U.S. Pat. No. 10,159,849), which is a continuation of U.S. patent application Ser. No. 14/579,615 (filed 22 Dec. 2014, now U.S. Pat. No. 9,925,387), which is a continuation of U.S. patent application Ser. No. 13/286,533 (filed 1 Nov. 2011, now U.S. Pat. No. 9,937,355), which claims the benefit of U.S. Provisional Patent Application 61/411,189 (filed 8 Nov. 2010). The disclosures of each of the foregoing applications are incorporated herein by reference in their entirety.

BACKGROUND OF THE INVENTION

1. Field of the Invention

The present invention is directed to a remote alarm for use with a wearable medical device.

2. Discussion of Related Art

During the course of use, a wearable medical device, such as a wearable defibrillator, a wearable insulin pump, etc., may issue audible alarms, voice prompts or messages, or visual messages to alert the patient or a bystander to a medical condition, to direct them to take some action to correct a problem, to call for assistance, to request information from the patient or the bystander, or to provide feedback to the device so that the device may continue to function properly. For example, where the wearable medical device is a wearable defibrillator, if the device determines that the patient is experiencing cardiac arrhythmia, the device may issue alarms and voice messages instructing the patient to indicate that they are conscious by pressing and holding a button associated with the device, thereby instructing the device to withhold the delivery of a defibrillating shock. If the patient does not respond, the device may presume that the patient is unconscious, and proceed with the treatment sequence, culminating in the delivery of one or more defibrillating shocks to the body of the patient. Alarms and messages may also be directed to a bystander instructing the bystander to call for medical assistance, or to alert any bystanders that a defibrillating shock is about to be delivered and to stand clear of the patient.

SUMMARY OF THE INVENTION

Applicants have appreciated that there may be circumstances where the alarms and messages may not be received by the patient or bystanders. For example, where the patient is asleep in bed, the patient may be sleeping so soundly that the alarms and voice messages are not loud enough to wake the patient. Alternatively or additionally, the speaker region of the wearable medical device may be blocked or shielded by bedding or an article of clothing, thereby reducing the sound to a level where the patient or bystander does not hear the alarms, voice prompts or messages. Even where the patient may be awake, the patient may be located in a noisy environment, such that they cannot hear the alarms or messages.

According to an aspect of the present invention, a remote alarm is provided for use with a wearable medical device. In accordance with one embodiment, the remote alarm is configured to receive alarms, voice messages and prompts issued by the wearable medical device and to repeat those alarms, voice messages and prompts in a manner that can more easily be perceived by a patient wearing the wearable medical device or a bystander. In accordance with another embodiment, the remote alarm can be configured to receive a communication from the wearable medical device, and in response to that communication, to identify one or more messages to be provided to the patient or a bystander. The messages may be provided audibly or visually, or both. In certain embodiments, in addition to providing messages to the patient or bystander, the remote alarm may further be configured to take certain actions depending upon the content of the communication, such as sending a telephone message to alert emergency personnel to the identity, location and medical condition of the patient, or sending an email to a friend or relative.

In accordance with one embodiment of the present invention, a remote alarm is provided for use with a wearable medical device. The remote alarm comprises an RF receiver to receive an RF signal indicative of a message to be provided by the wearable medical device, an audio circuit, electrically coupled to the receiver, to convert the message to an audio signal, and an audio display device. The audio display device is electrically coupled to the audio circuit to receive the audio signal and reproduce the message to be provided by the wearable medical device. In accordance with an aspect of this embodiment, the receiver receives the RF signal using one of a Bluetooth, Wireless USB, and a ZigBee communication standard, and the message is a voice message, siren, or tone. In accordance with another aspect of this embodiment, the wearable medical device is a wearable defibrillator. In accordance with a further aspect of this embodiment, the message is reproduced at a greater volume than can be provided by the wearable medical device. In accordance with a further aspect of this embodiment, the remote alarm includes a high intensity light bulb that illuminates in response to receipt of the message.

In one embodiment, the RF receiver, the audio circuit, the audio display device, and the light bulb are integrated into a first device configured to be directly plugged into an AC power receptacle. In a further embodiment, the remote alarm further comprises a second device, distinct from the first device, wherein the second device includes a response button by which a response to the message can be provided, and an RF transmitter to transmit the response to the wearable medical device. In a still further embodiment, the remote alarm may further comprise a third device, distinct from the first device and the second device, the third device including an RF receiver to receive the RF signal indicative of the message to be provided by the wearable medical device, and an electromechanical vibrator configured to vibrate in response to receipt of the message.

In accordance with another embodiment of the present invention, a remote alarm for use with a wearable medical device is provided. The remote alarm comprises an RF transceiver to receive an RF communication from the wearable medical device, a processor, an audio circuit, and an audio display device. The processor is electrically coupled to the RF transceiver to process the communication and to identify a message based upon a content of the communication. The audio circuit is electrically coupled to the processor and configured to convert the message to an audio signal, and the audio display device is electrically coupled to the audio circuit and configured to audibly reproduce the message. In accordance with one aspect of this embodiment, the message may include a text message, and the audio circuit includes a voice synthesizer that is configured to convert the text message to an audio signal, that when reproduced by the audio display device, corresponds to a speech version of the text message.

In accordance with another aspect of this embodiment, the message is a first message, and the remote alarm further comprises at least one communication interface that is electrically coupled to the processor and communicatively coupled to a network. The at least one communication interface is configured to communicate a second message over the network in response to receipt of the communication. In accordance with a further aspect of this embodiment, in response to the content of the communication indicating that a patient wearing the wearable medical device is experiencing a medical condition, the processor is configured to instruct the at least one communication interface to send the second message over the network to emergency personnel. In accordance with an aspect of this embodiment, the at least one communication interface includes at least one of a telephone network interface, a computer network interface, and a cellular network interface. In accordance with another aspect of this embodiment, the processor instructs the at least one communication interface to communicate the second message over the network to emergency personnel responsive to the content of the communication indicating that a patient wearing the wearable medical device is experiencing a medical emergency. In accordance with a further aspect of this embodiment, the second message identifies the patient, a physical location of the patient, and the medical emergency.

In accordance with yet another aspect of this embodiment, the processor further instruct the at least one communication interface to communicate a third message over the network to at least one of a caregiver of the patient and a relative of the patient. In accordance with an aspect of the present invention, the wearable medical device can be a wearable defibrillator.

In accordance with a still further aspect of this embodiment, the remote alarm may include additional circuitry capable of performing other functions, such as a user interface to receive feedback from the patient or a bystander, and a battery charging and conditioning circuit to receive, charge, and condition a rechargeable battery of the wearable medical device. In certain embodiments, feedback received from the patient or a bystander may be transmitted to the wearable medical device. For example, in one embodiment, the remote alarm further comprises a user interface, electrically coupled to the processor. In this embodiment, the user interface is configured to receive a response to the message, and the processor send the response to the wearable medical device via the RF transceiver in response to receipt of the response to the message by the user interface. In accordance with a further aspect of this embodiment, the message is a first message, and the remote alarm further comprise at least one communication interface that is electrically coupled to the processor and communicatively coupled to a network, the at least one communication interface being configured to communicate a second message over the network in response to receipt of the communication. In accordance with one embodiment, in response to the content of the communication indicating that a patient wearing the wearable medical device is experiencing a medical emergency, and responsive to the remote alarm not receiving any response to the message, the processor instructs the at least one communication interface to communicate the second message over the network to emergency personnel, the second message identifying at least one of the patient, a physical location of the patient, and the medical emergency.

In accordance with one embodiment, the remote alarm includes a clip configured to secure the remote alarm to an ear of a patient wearing the wearable medical device, and in accordance with another embodiment, the remote alarm includes a strap configured to secure the remote alarm to a wrist of a patient wearing the wearable medical device.

In accordance with another aspect of the present invention, a method of remotely alerting a patient wearing a wearable medical device to a medical condition is provided. The method comprises acts of receiving, on a first device that is distinct from the wearable medical device, a communication from the wearable medical device; processing, on the first device, the communication to identify a message to be communicated to the patient based upon a content of the communication; determining, on the first device, whether the message is to be immediately communicated to the patient; and converting the message to an audio signal and audibly reproducing the message on the first device to alert the patient to the medical condition in response to a determination that the message is to be immediately communicated to the patient.

In accordance with one embodiment, the message is a first message, and the method further comprising acts of waiting, responsive to the act of converting and audibly reproducing the first message, a predetermined period of time for a response to the first message; and communicating, over a communication network to which the first device is communicatively coupled, a second message to at least one of emergency medical personnel, a caregiver of the patient, and a relative of the patient to alert them to the medical condition in response to not receiving the response to the first message within the predetermined period of time.

In accordance with another embodiment, the method further comprises acts of converting the message to a text message in response to a determination that the message is not to be immediately communicated to the patient; storing the text message in a memory of the first device; and setting an indicator on the first device to alert the patient to the stored text message.

In accordance with yet another embodiment, the message is a first message, and the method further comprises an act of sending a second message from the first device to a second device that is distinct from the first device and the wearable medical device, the second message instructing the second device to vibrate in response to receipt of the second message to alert the patient to the medical condition.

Still other aspects, embodiments, and advantages of these exemplary aspects and embodiments, are discussed in detail below. Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearance of such terms herein is not necessarily all referring to the same embodiment.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
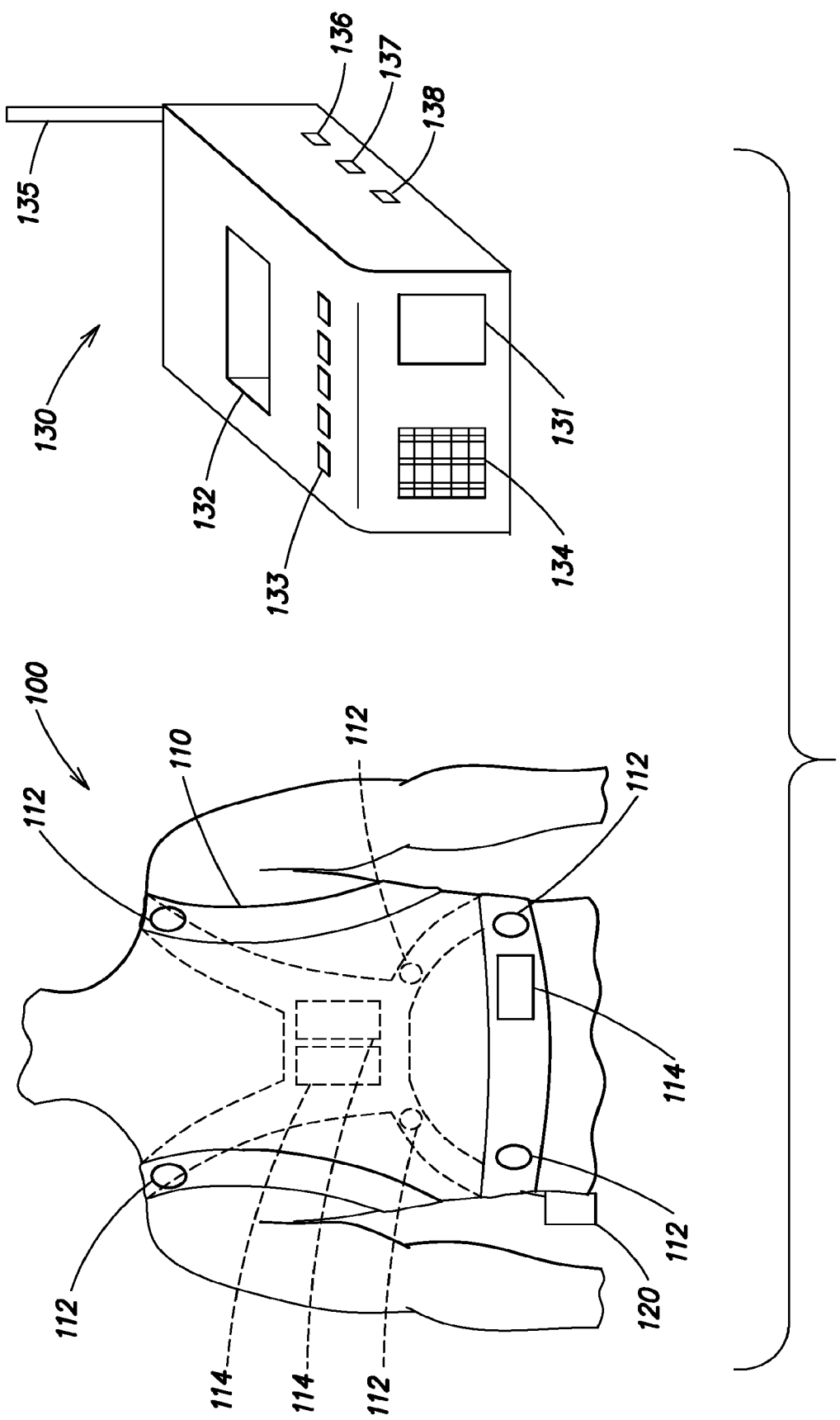
FIG. 1 illustrates a wearable medical device, such as a wearable defibrillator and an associated base unit.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

FIG. 1 illustrates a wearable medical device 100 and an associated base unit 130. In the embodiment depicted in FIG. 1, the wearable medical device 100 is a wearable defibrillator, such as a LifeVest® wearable cardioverter defibrillator available from Zoll Medical Corporation of Chelmsford, Mass. As shown, the wearable medical device 100 includes a harness 110 having a pair of shoulder straps and a belt that is worn about the torso of a patient. The wearable medical device 100 includes a plurality of ECG sensing electrodes 112 that are attached to the harness 110 at various positions and electrically coupled to a control unit 120. The wearable medical device 100 also includes a plurality of therapy electrodes 114 that are electrically coupled to the control unit and capable of delivering one or more therapeutic defibrillating shocks to the body of the patient, if it is determined that such treatment is warranted. Although not shown, the wearable medical device 100 may include additional sensors, other than the ECG sensing electrodes 112, capable of monitoring the physiological condition or activity of the patient. For example, sensors capable of measuring blood pressure, heart rate, thoracic impedance, pulse oxygen level, respiration rate, heart sounds, and the activity level of the patient may also be provided.

In use, the control unit 120 of the wearable medical device 100 monitors ECG signals provided by the plurality of ECG electrodes 112 and, where provided, some or all of the signals provided by other sensors. Where the control unit 120 determines that the patient is experiencing cardiac arrhythmia, the control unit 120 may issue an audible alarm via a loudspeaker (not shown) on the control unit 120 or on the harness 110 alerting the patient and any bystanders to the patient's medical condition. The control unit 120 may also instruct the patient to press and hold a button (not shown) on the control unit 120 or elsewhere to indicate that the patient is conscious, thereby instructing the control unit 120 to withhold the delivery of one or more therapeutic defibrillating shocks.

As shown in FIG. 1, the wearable medical device 100 may be associated with a base unit 130. For example, in the LifeVest® wearable cardioverter defibrillator, a base unit 130 is provided that is capable of performing a number of different functions. One of the functions performed by the base unit 130 is to charge an auxiliary battery that is used to provide power to the wearable medical device. The LifeVest® wearable cardioverter defibrillator is provided with two batteries, such that one of the batteries is recharged while the other is providing power to the device. When the battery that is providing power to the device needs recharging, it is swapped with the auxiliary battery, and recharged, with this cycle being repeated throughout the duration of patient usage. Another of the functions performed by the base unit 130 is to store and/or communicate information received from the wearable medical device over a wired or wireless communication network. For example, information relating to the patient's medical condition over a period of time may be communicated by the base unit 130 to a medical service provider, such as a doctor, so that the doctor may remotely monitor the patient's medical condition. The information received by the base unit 130 may be communicated over the network shortly after it is received by the base unit 130, or alternatively, may be stored in a memory of the base unit 130 and communicated over the network at a later time. The information that is communicated by the base unit 130 may be retained in the memory of the base unit.

The base unit 130 includes a visual display 131 that can communicate visual messages to the patient or a bystander, an audio output device 134, such as a loudspeaker, that can communicate audible messages to the patient or a bystander, and a plurality of buttons 133 by which the patient or a bystander can communicate with the base unit 130. In certain embodiments, the visual display 131 may include a touch screen display, such that the patient or a bystander may also communicate with the base unit via the visual display 131. The base unit 130 includes at least one charging bay 132 to receive a rechargeable auxiliary battery, such as a three cell 2200 mAh lithium ion battery pack, that can be used to provide power to the wearable medical device 100. The base unit 130 also includes several different communication interfaces including: a device communication interface 138 to receive information from the control unit 120 of the wearable medical device, a telephone network interface 136 to communicate, via a telephone network, the information received from the wearable medical device, and a network interface 137 to communicate, via a wired network connection, the information received from the wearable medical device. In certain embodiments, the base unit 130 also includes an antenna 135 that can wirelessly communicate the information received from the wearable medical device via a cellular (e.g., 2G, 3G, and 4G) network.

Figure 2:
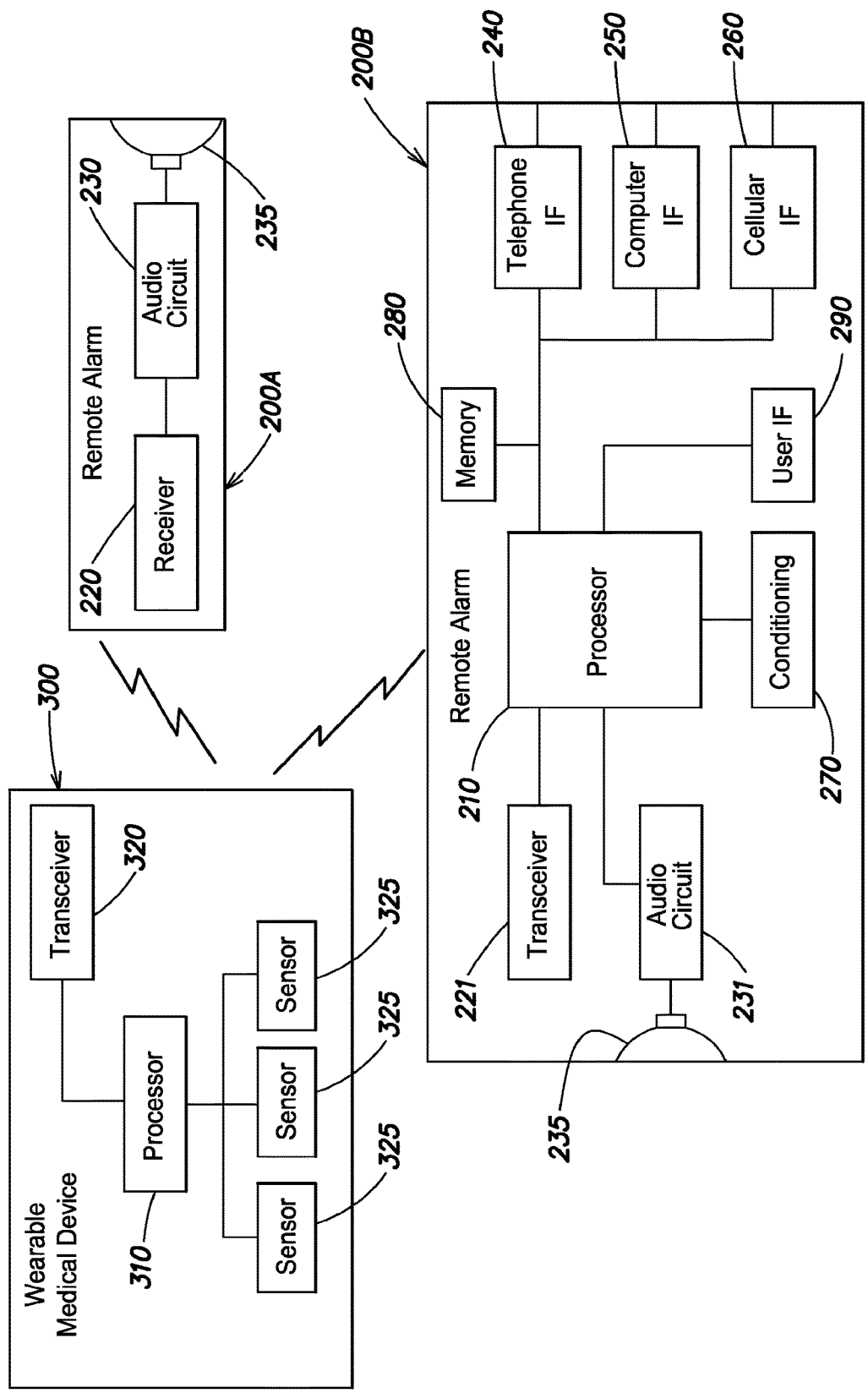
FIG. 2 is a functional block diagram of remote alarm that may be used with a wearable medical device in accordance with an aspect of the present invention.

FIG. 2 illustrates a remote alarm 200A, 200B that may be used with a wearable medical device 300, such as a wearable defibrillator, a wearable insulin infusion pump, or any other type of wearable medical device in accordance with an aspect of the present invention. The wearable medical device 300 generally includes at least one processor, microprocessor, or controller 310, such as a processor commercially available from companies such as Texas Instruments, Intel, AMD, Sun, IBM, Motorola, Freescale and ARM Holdings. In one exemplary embodiment directed to a wearable defibrillator, the at least one processor 310 may include a power conserving processor arrangement that includes a general purpose processor, such as an Intel® PXA270 processor and a special purpose processor, such as a Freescale DSP56311 Digital Signal Processor, as described in co-pending application Ser. No. 12/833,096, entitled SYSTEM AND METHOD FOR CONSERVING POWER IN A MEDICAL DEVICE, filed Jul. 9, 2010 (hereinafter the "'096 application") and incorporated by reference herein in its entirety. The at least one processor 310 is electrically coupled to a plurality of sensors 325, such as ECG sensing electrodes 112 and therapy electrodes 114 (FIG. 1) to monitor the patient's medical condition, and in some embodiments, to provide medical treatment to the patient in response to a detected medical condition, such as cardiac arrhythmia.

In accordance with an aspect of the present invention, the wearable medical device 300 also includes a wireless Radio Frequency (RF) transceiver 320 that is electrically coupled to the at least one processor 310 and capable of wirelessly and bi-directionally communicating with the remote alarm 200A, 200B. In certain embodiments, the wireless RF transceiver 320 may communicate with the remote alarm 200A, 200B using a wireless communication standard and protocol that is optimized for low cost and shorter distance (e.g., 10 meters) communications, such as Bluetooth, Wireless USB, or ZigBee. In other embodiments, the RF transceiver 320 may communicate with the remote alarm 200A, 200B using a communication standard and protocol capable of communicating over greater distances, such as Wireless Ethernet, or GSM. For example, in one embodiment, the RF transceiver 320 may communicate via wireless Ethernet with a large format display device, such as a television or an Ipad® to display status, alerts or reminders communicated by the wearable medical device. In certain embodiments, where low cost is a concern, or where communication in only one direction is desired, the wireless RF transceiver 320 may be replaced with a wireless RF transmitter capable of transmitting an analog signal. Although the wearable medical device 300 would not be able to receive messages from the remote alarm 200A, 200B, this embodiment would still be capable of sending information to the remote alarm over a wireless communication channel as discussed further below.

In accordance with one embodiment of the present invention, the remote alarm 200A, 200B may be implemented as a low-cost device with a singular purpose of being a remote bed-side or table-top alarm that is capable of repeating alarms, voice prompts, and messages issued by the wearable medical device. A functional block diagram of such a single purpose, low-cost, remote alarm is identified in FIG. 2 by reference designator 200A. In an alternative embodiment, the remote alarm 200A, 200B may include additional functionality, such as, for example, the ability to receive, charge and condition one or more auxiliary rechargeable batteries, the ability to function as an alarm clock, the ability to receive and store information indicative of the patient's medical condition, the ability to communicate information, including information indicative of the patient's medical condition, to a medical service provider, to a friend or relative, or to emergency personnel over a wired, wireless, or telephone network, etc. A functional block diagram of such a multi-function remote alarm is identified in FIG. 2 by reference designator 200B. Each of these embodiments is now described in detail below.

The remote alarm 200A includes a wireless RF receiver 220 that is electrically coupled to an audio circuit 230, which is, in turn, electrically coupled to an audio output device 235, such as a loudspeaker. The wireless RF receiver 220 is capable of receiving an analog RF signal from the wearable medical device 300 that carries the same information as that which would be provided to audio circuitry included in the wearable medical device. The information received by the RF receiver 220 is provided to the audio circuit 230 that converts the received information to an audio signal capable of being reproduced by the audio output device 235. In this embodiment, the remote alarm 200A simply repeats the same alarms, voice prompts, and voice messages that would be provided by the wearable medical device 300. However, because the remote alarm 200A may be placed in a location where it will not be blocked by bedding, clothing, or other obstructions, and because the audio output device can be larger than that on the wearable medical device, the sound emitted by the remote alarm 200A will be louder than that provided by the wearable medical device 300 and more likely to be heard by the patient or any bystander. It should be appreciated that rather than transmitting an analog RF signal to the remote alarm 200A, a digital RF signal may be used instead. However, the use of digital communication may require additional circuitry, such as a Digital-to-Analog converter, which may be avoided by using an analog RF transmission where cost is a paramount concern.

The remote alarm 200B is capable of performing functions in addition to those described with respect to remote alarm 200A, and may be integrated into a base unit, such as the base unit 130 described with respect to FIG. 1. The remote alarm 200B includes a processor 210 that is electrically coupled to a wireless RF transceiver 221 and an audio circuit 231, with the audio circuit 231 being electrically coupled to an audio output device 235, such as a loudspeaker. The remote alarm 200B also includes a memory 280, such as RAM, ROM, or Flash memory that is electrically coupled to the processor 210. Although the memory 280 is shown as being separate from the processor, it should be appreciated that certain commercially available processors may include the memory on the same integrated circuit as the processor 210. Moreover, the memory 280 may include other types of memory, such as magnetic disk memory, optical memory, a USB jump drive, etc. The processor 210 may be any general purpose or special purpose processor available from companies such as Texas Instruments, Intel, Sun, AMD, IBM, Motorola, etc.

The wireless RF transceiver 221 is capable of wirelessly and bi-directionally communicating with the wearable medical device 300, and may include any type of transceiver that is compatible with the communication standard and protocol used by the transceiver 320 of the wireless medical device 300, such as Bluetooth, Wireless USB, ZigBee, etc. In certain embodiments, where low cost is a concern, or where communication in only one direction is desired, the wireless RF transceiver 221 may be replaced with a wireless RF receiver, such as that described above with respect to remote alarm 200A, such that the remote alarm 200B can receive messages and alarms transmitted by the wearable medical device, but cannot send communications back to the wearable medical device 300. The audio circuit 231 may be any audio circuit capable of providing an audio signal to the audio output device 235. In certain embodiments, the audio circuit 231 may include a voice synthesizer capable of converting text messages to audible voice messages.

In accordance with certain embodiments of the present invention, the remote alarm 200B may include additional circuitry to implement additional functionality. For example, the remote alarm 200B may include a plurality of communication interfaces, such as a telephone network interface 240 by which the remote alarm 200B can communicate over a telephone network, a wired or wireless computer network interface 250 by which the remote alarm 200B can communicate over a computer network, and a cellular network interface 260 by which the remote alarm 200B can communicate over a cellular (e.g., 2G, 3G, 4G) network. Other circuitry that may be included in the remote alarm 200B may include a battery recharging and conditioning circuit 270 capable of conditioning and recharging one or more rechargeable batteries that can be used to provide power to the wearable medical device 300, and a user interface 290. The user interface 290 may include a visual touch screen display by which the patient or a bystander can communicate with the remote alarm 200B, and may include a plurality of buttons and/or LEDs, or even a computer keyboard connector for attachment of a computer keyboard to the remote alarm 200B. The visual touch screen display may function as a clock or as an alarm clock when not otherwise communicating with the patient or a bystander, or alternatively, a separate display may be provided to implement alarm clock functionality.

In accordance with one embodiment of the present invention, the functionality of the remote alarm 200B may be similar to that provided by the wearable medical device 300. For example, in one embodiment, the remote alarm 200B may receive the same information provided to audio circuitry on the wearable medical device 300 and simply repeat those alarms, voice messages, and voice prompts. Where the patient or bystander does not respond, the remote alarm may be programmed to repeat the alarm, voice message, or prompt, but at a louder volume. Such functionality may be sufficient to get the patient's attention, even where the patient is located in a noisy environment, asleep, or both.

In accordance with another embodiment of the present invention, the remote alarm 200B can be capable of providing feedback to the wearable medical device 300. For example, in one embodiment, in response to an alarm, voice message or prompt, the patient or a bystander may communicate with the wearable medical device 300 via the user interface 290 on the remote alarm 200B. The patient could thereby acknowledge that the alarm, voice prompt, or voice message was received by pressing a button on the remote alarm 200B, or by interacting with the touch screen on the remote alarm. The remote alarm 200B could then transmit that acknowledgement to the wearable medical device 300 via the transceiver 221. In certain embodiments, the remote alarm 200B can include software and/or hardware capable of determining whether the acknowledgement of the alarm, voice prompt, or message is provided by the patient, or by another. For example, the remote alarm 200B can include voice recognition functionality capable of recognizing the patient's voice, or that of a loved one or caretaker as described in co-pending U.S. patent application Ser. No. 12/082,168, entitled WEARABLE DEFIBRILLATOR WITH AUDIO INPUT/OUTPUT, which is herein incorporated by reference in its entirety. Alternatively, the remote alarm 200B can include hardware and/or software to recognize biometric information of the patient (or that of a loved one or caretaker), such as capacitance, ECG signals, or markers or ID signals, as described in co-pending U.S. patent application Ser. No. 12/150,720, entitled MEDICAL DEVICE CONFIGURED TO TEST FOR USER RESPONSIVENESS, which is herein incorporated by reference in its entirety.

In accordance with another embodiment of the present invention, the remote alarm 200B can be capable of providing enhanced communications relative to those afforded by the wearable device 300. For example, rather than transmitting the same information to the remote alarm 200B that wearable medical device 300 provides to its audio circuitry, the wearable device 300 could communicate a code to the remote alarm 200B that corresponds to a particular alarm, message, or prompt stored in a message table in the memory 280 of the remote alarm 200B. The code transmitted to the remote alarm 200B could be in analog form, or digital. On receipt of the code, the processor 210 could access the message table and communicate the message to the patient or bystander. The message could be stored in the message table in text form and converted to speech by a voice synthesizer in the audio circuit 231 of the remote alarm 200B. Alternatively, the message could be displayed in text form on the touch screen display, either alone, or in combination with the message being reproduced audibly. The code could identify the content and or length of the message, prompt or alarm to be communicated to the patient or bystander, as well as the loudness of the message, and what actions are to be taken in the event of a particular response, or lack of response, from the patient or bystander.

For example, where the wearable medical device 300 is a wearable defibrillator, in the event that the wearable medical device detects a cardiac arrhythmia and the patient does not respond to indicate they are conscious, the remote alarm 200B can place a phone call to emergency personnel (e.g., 911). The remote alarm 200B can then play a pre-recorded message that may be stored in the memory 280 to identify the name of the patient, their location, and the detected medical condition. The remote alarm 200B can also notify the patient's medical service provider to alert them to the patient's condition and that emergency services have been called, and also inform a loved one or relative. The names of the various contacts and the content of the messages to be sent can be stored in the memory 280 of the remote alarm 200B during a set-up procedure. The patient's medical service provider and the patient's loved one or relative can be sent an email or text message via the wired or wireless computer network interface 250, or contacted by telephone after notifying emergency personal using either the telephone network interface 240 or the cellular network interface 260 and playing a pre-recorded message.

Other enhanced communications that may be provided by the remote alarm 200B can include the ability to communicate messages in different languages. For example, the user interface 290 of the remote alarm 200B can permit a first language (e.g., the patient's native language) to be selected and used for communicating with the patient, and a second language, different than the first language, to be selected and used for communicating with others, such as bystanders or emergency personnel. Such a feature would be appropriate for those instances where the patient speaks one language, but is physically present in a geographic location where the language spoken by the patient is not native to the geographic location. Where the remote alarm 200B includes an ability to detect its geographic location (e.g., GPS capability), the remote alarm may automatically configure itself to use the language native to that geographic location for communications directed to a bystander or emergency service personnel.

In accordance with one embodiment, the remote alarm 200B is capable of communicating various information to the patient, a bystander, a caregiver or a loved one in different ways, depending on the type of information being communicated, or depending on the manner in which the remote alarm is programmed to communicate such information. For example, where the information to be communicated to the patient is of an urgent nature, the remote alarm 200B may immediately communicate this information to the patient via the audio output device 235, alone or in combination with other types of notification (e.g., by energizing a vibrating alarm disposed on or near the patient's body as discussed further below). Where the wearable medical device 300 is a wearable defibrillator, such information that may be considered to be of an urgent nature can include a warning message of imminent shock based upon a detected arrhythmia, a warning message identifying that the rechargeable battery that is powering the wearable medical device 300 is critically low on charge, a warning message that a sufficient number of sensors have fallen off or lost contact with the patient's body such that the patient may not be protected, etc. Where no response is provided by the patient, the remote alarm may increase the volume of the alarm, voice message, or prompt, as well as perhaps notify emergency personnel, a caregiver, or a loved one. Where the patient is mentally impaired, alarms or other messages may be communicated immediately to a caregiver.

Alternatively, where the information to be communicated to the patient is important, but not of an urgent nature, other forms of communication may be more appropriate. For example, where the wearable medical device 300 is a wearable defibrillator and the information to be communicated to the patient corresponds to a detected arrhythmia that abated before a warning message of imminent shock was to be delivered, the remote alarm may simply store the information in the memory 280 and set an indicator (e.g., such as an LED) of the user interface 290 to prompt the patient to interface with the remote alarm 200B and retrieve that information when next possible. Even where an arrhythmia was detected and a therapeutic shock delivered, the patient may be unaware of this fact. By being prompted to retrieve such information, the patient may be made aware of such events. The occurrence of such events may also be communicated, for example via email, text, or voicemail to the patient, a loved one, a caregiver, or a medical service provider to alert them to the occurrence of the event. Other types of information that may be important but not urgent for a wearable defibrillator to communicate to the patient (or a caregiver) can include a poor signal to noise ratio on one or more sensors (but fewer than a sufficient number of sensors needed to protect the patient), a detected fall-off of one or more sensors (but again, fewer than a sufficient number of sensors), a low battery condition that is not below that needed to monitor and protect the patient, a warning that the harness 110 (FIG. 1) of the wearable medical device may need to be laundered to restore its fit, etc. For other types of wearable medical devices, including defibrillators, messages that are important, but perhaps not urgent, can include reminders about taking medications, a reminder to take a blood glucose reading at a particular time, a reminder to change a battery or a notification that a normal battery replacement or change time has been missed, etc.

In accordance with an aspect of the present invention, the patient or a caregiver may use the user interface to set what types of messages should be communicated immediately versus those that can wait till the next time the patient interacts with the remote alarm. Such settings may be modified based on the time of day and the patient's schedule. For example, those messages that might not be necessary to be communicated immediately when the patient is asleep may be programmed to be communicated immediately where the time of day is such that the user would be awake. Via the user interface, the patient, a caregiver, a medical service provider, or a service technician may set reminders to take medication, reminders to change or recharge a battery, etc., and assign a priority rating to each type of event. Default settings may be provided, that may be altered via the user interface 290. Other settings may be provided to indicate whether the communication should be audible, tactile, or both, and whether people other than the patient (e.g., a loved one or caregiver) should be notified.

In accordance with a further aspect of the present invention, information may be pushed to the remote alarm by the patient's caregiver, by the patient's medical service provider, by a loved one, or by a service organization associated with the wearable medical device. For example, where the service organization or manufacturer of the wearable medical device has a message about the device for the patient (e.g., a product recall, a product update, etc.), a message may be pushed to the device for later review by the patient at the next possible timeframe. Alternatively, a message from the patient's medical service provider or a loved one may be pushed to the remote alarm, such as, for example, a reminder about a medical appointment, etc.

Figure 3:
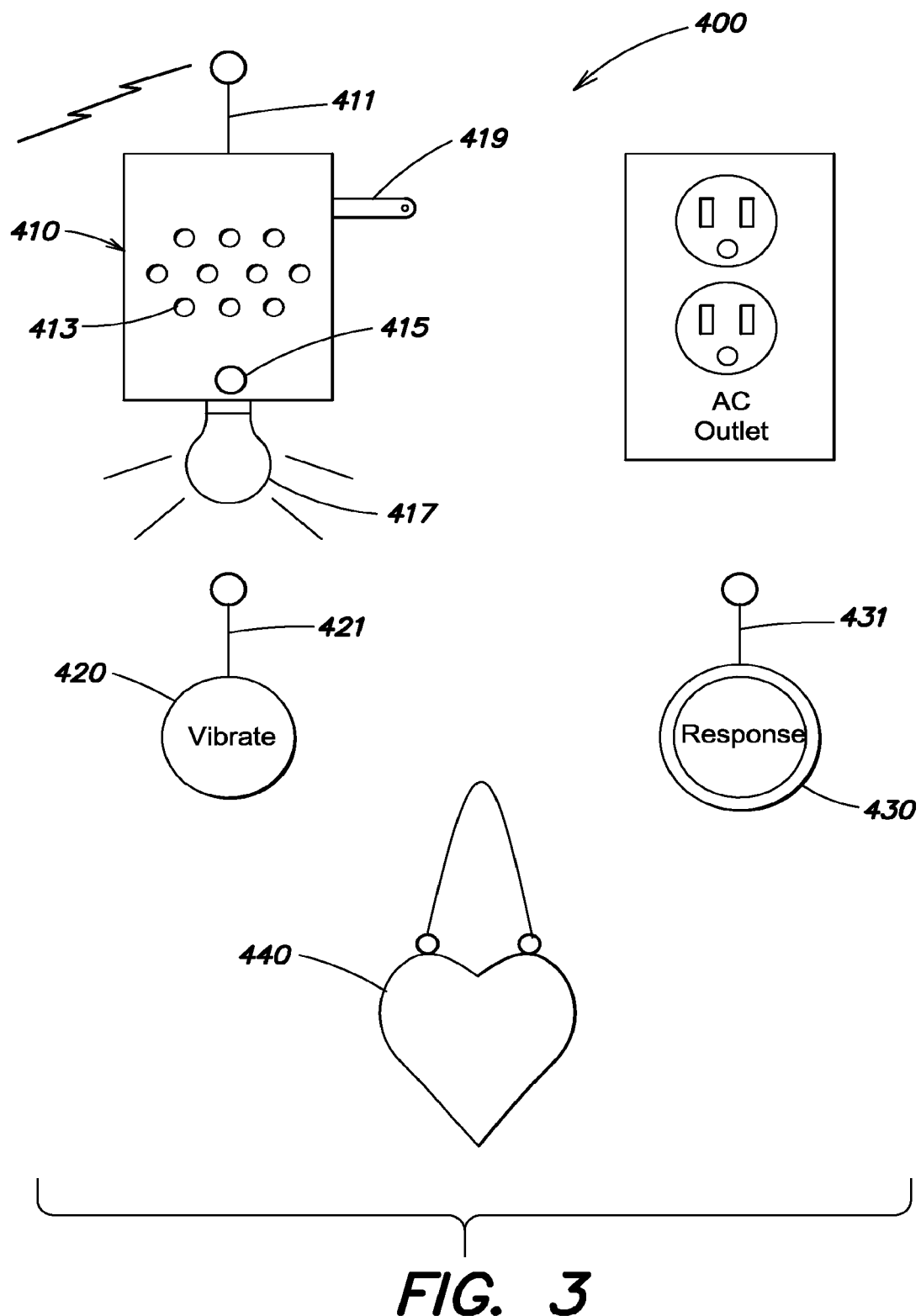
FIG. 3 illustrates a remote alarm that may be used with a wearable medical device in accordance with an aspect of the present invention in which the remote alarm includes a number of discrete alarm devices.

Although each of the remote alarms 200A, 200B has been described herein as including an RF receiver 220 or transceiver 221 to receive an RF signal from the wearable medical device 300, it should be appreciated the present invention is not so limited. For example, in an alternate embodiment, the remote alarm may simply include a microphone capable of receiving alarms, voice prompts and messages issued by the wearable medical device and an audio circuit and speaker capable of repeating those alarms, voice prompts and messages, for example, at a louder volume. Alternatively still, the communication between the wearable medical device 300 and the remote alarm 200A, 200B could be infrared, audio, or sub-audio. Moreover, although the remote alarms 200A, 200B are shown as integrated devices, it should be appreciated that various functionality of the remote alarms 200A, 200B may be distributed amongst various individual devices that together provide the described functionality. For example, FIG. 3 illustrates a remote alarm 400 that includes a number of discrete devices 410, 420, 430, and 440 that may collectively operate as a remote alarm. As shown in FIG. 3, in one embodiment, the remote alarm 400 includes an AC receptacle alarm unit 410 that is configured to be plugged directly into a conventional wall power outlet, a vibrating alarm unit 420 that is configured to be placed adjacent to the patient in the patient's bed or armchair, or beneath the mattress of the patient's bed or a seat or back cushion of the patient's armchair, a remote response button 430 that is configured to be placed in any location convenient for the patient, such as on the nightstand next to the patient's bed, or adjacent the patient, and an alarm pendant 440 that is configured to be worn by a loved one or a caregiver of the patient.

As shown in FIG. 3, the AC receptacle alarm unit 410 includes an RF antenna 411 by which it can receive messages from the wearable device 300 and transmit information back to the wearable device. Although not shown, the AC receptacle alarm unit 410 may include a second antenna capable of communicating (e.g., via a cellular or wireless network) with a medical service provider or emergency personnel. The AC receptacle alarm unit 410 also includes an audio output device 413, such as a loudspeaker, an audio input device 415, such as a microphone, a light 417, and a plurality of contacts 419 configured to be received in the wall power outlet. It should be appreciated that the AC receptacle alarm unit may be modified for use with a DC wall outlet. In accordance with an aspect of this embodiment, in response to an urgent message requiring the immediate attention of the patient or another, the AC receptacle alarm unit 410 may not only audibly communicate the message, but may also illuminate the light 417, which may be a high intensity light bright enough to awaken a sleeping patient (e.g., equivalent in intensity to a 60 watt incandescent bulb, or greater). Although not shown, the AC receptacle alarm unit 410 may include a charging bay capable of receiving and charging an auxiliary battery unit.

The vibrating alarm unit 420 is configured to be placed adjacent the patient, or in any other location (such as beneath a mattress upon which the patient sleeps, or beneath or behind a cushion of an arm chair in which the patient reposes) where its vibration would be likely to alert the patient, if the patient is conscious. The vibrating alarm unit 410 includes an antenna 421 to receive information from the wearable ambulatory device 300 (FIG. 2), and/or the AC receptacle alarm unit 410, and an electro-mechanical vibrator, such as a piezoelectric vibrator.

The remote response button 430 is configured to be disposed in any convenient location where the patient can access the remote response button, and thereby send a signal to the wearable medical device indicating that the patient is conscious. As shown, the remote response button 430 includes an antenna 431 for receiving communications from the wearable medical device or the AC receptacle alarm unit 410, and for transmitting a signal to the wearable device and/or the AC receptacle alarm unit indicating the patient's consciousness. Although not shown, the remote response button 430 may include an audio output device, such as a loudspeaker, and audio circuitry to repeat the same alarms, voice prompts, and voice messages that would be provided by the wearable medical device. Although the remote response button 430 is described as being one of the discrete devices of the remote alarm 400, it should be appreciated that both the remote response button 430 and the AC receptacle alarm unit 410 may be used as standalone devices.

The alarm pendant 440 is configured to be worn about the neck of a caregiver or loved one, and may light, vibrate, or emit an audible sound alerting the caregiver to check on the patient in the event that an event requiring their attention has been detected. Although not shown, the alarm pendent would also include an RF antenna capable of receiving RF communications, such as Bluetooth, Wireless USB, or ZigBee.

Figure 4:
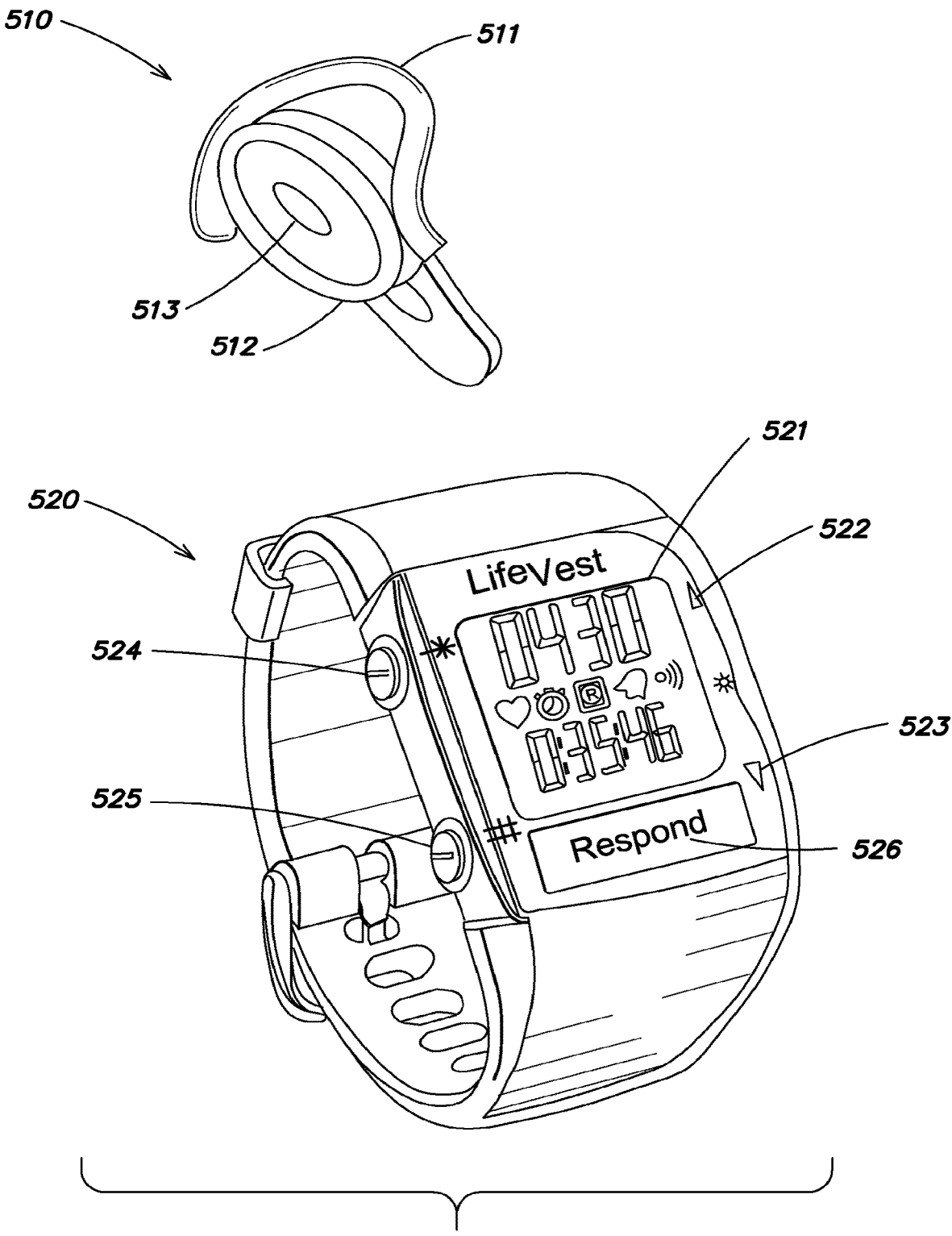
FIG. 4 illustrates several alternative embodiments of a remote alarm in accordance with aspects of the present invention.

FIG. 4 illustrates two alternative embodiments of a remote alarm in accordance with aspects of the present invention in the form of an earpiece remote alarm 510 and a watch monitor remote alarm 520. The earpiece remote alarm 510 includes a clip 511 configured to be disposed about the patient's ear, and a control module 512 that includes an RF transceiver, such as a Bluetooth transceiver. Although not visible, in FIG. 4, the earpiece remote alarm 510 includes an audio output device, such as a speaker configured to be disposed proximate the patient's ear canal for audibly communicating messages received from the wearable medical device 300 to the patient. The earpiece remote alarm may further include a microphone, such that the earpiece remote alarm may additionally act as a hearing aid in which sounds received by the microphone are amplified and conveyed to the patient. As the human ear is considered to be a relatively good location at which to measure the pulse oxygen level of a patient, the earpiece remote alarm 510 may include a pulse oxygen sensor (not shown) that monitors the patient's pulse oxygen level and communicates this information to the wearable medical device 300 (FIG. 2). In some embodiments, the earpiece remote alarm may include a response button 513 by which the patient may indicate their consciousness in response to a detected cardiac arrhythmia and warning of imminent shock.

The watch monitor remote alarm 520 resembles an ordinary wristwatch and is configured to be disposed about the patient's wrist using a strap in a conventional manner. The watch monitor remote alarm may, for example, be based upon a watch monitor reference platform, such as the eZ430 Chronos Wireless Watch, available from Texas Instruments. As shown, the watch monitor remote alarm 520 includes a display 521 which can display the date and time, and operate as a conventional wristwatch/alarm using, for example, buttons 524 and 525 for programming the date and time, and setting any alarms. The display 521 can also display informational messages or prompts communicated by the wearable medical device 300 (FIG. 2). For example, as shown in FIG. 4, the display 521 may display a heart symbol to indicate that no arrhythmias are currently detected, and may indicate the state of charge of the battery unit associated with the wearable medical device. Although not shown, the watch monitor remote alarm 520 may include an RF transceiver to receive messages, prompts, and other information from the wearable medical device 300, and to communicate information back to the wearable medical device. For example, where the wearable medical device detects a cardiac arrhythmia and issues a warning that a shock is imminent, the patient may press and hold a response button 526 to indicate that they are conscious. The watch monitor remote alarm 520 may again include functionality to determine whether the response button 526 was actuated by the patient, or by another. Communication standards supported by the watch monitor remote alarm can include Bluetooth, Wireless USB, ZigBee, as well as wireless Ethernet. The watch monitor remote alarm 520 can include an audio output device (not shown) by which alarms or audible messages may be communicated to the patient. The watch monitor remote alarm may also include sensors (disposed on the back side of the watch and not visible in FIG. 4) to detect the patient's pulse rate, temperature, or blood oxygen level, which may be displayed on the display 521. Such information may be displayed by using scrolling buttons 522 and 523.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A cardiac monitoring and treatment system for providing medical or device notifications to a patient, the system comprising:
    a wearable cardioverter defibrillator worn by the patient, the wearable cardioverter defibrillator configured to detect a treatable cardiac condition in the patient and deliver a therapeutic shock to treat the treatable cardiac condition, wherein the wearable cardioverter defibrillator comprises a first response button that, when actuated, causes the wearable cardioverter defibrillator to withhold delivery of the therapeutic shock; and a remote device comprising
- a memory,
- a communication interface configured to communicate bidirectionally with the wearable cardioverter defibrillator,
- an audio output device,
- a second response button that, when actuated, causes the wearable cardioverter defibrillator to withhold delivery of the therapeutic shock to the patient, and
- a processor that is coupled to the memory, the communication interface, the audio output device, and the second response button, wherein the processor is programmed to
  - receive a communication from the wearable cardioverter defibrillator,
  - determine whether the received communication is an urgent communication, and
  - in response to determining that the received communication is an urgent communication, cause the audio output device to provide a notification based on the received communication.

2. The system of claim 1, wherein the processor of the remote device is programmed to, in response to determining that the received communication is not an urgent communication, store the received communication in the memory.

3. The system of claim 2, wherein:
the remote device further comprises a visual indicator; and
the processor is further programmed to, in response to determining that the received communication is not an urgent communication, activate the visual indicator to indicate to the patient that the communication was received.

4. The system of claim 1, wherein the remote device is configured to repeat a message issued by the wearable cardioverter defibrillator.

5. The system of claim 4, wherein the message is an alarm issued by the wearable cardioverter defibrillator, and wherein the audio output device is configured to repeat the message at a louder volume.

6. The system of claim 1, wherein the processor is configured to determine that the received communication is an urgent communication that was generated in response to the wearable cardioverter defibrillator detecting the treatable cardiac condition.

7. The system of claim 6, wherein the notification comprises instructions to the patient to actuate at least one of the first and second response buttons to indicate that the patient is conscious.

8. The system of claim 7, wherein the processor is configured to cause the audio output device to provide the notification immediately upon determining that the received communication is an urgent communication.

9. The system of claim 6, wherein the notification comprises instructions to the patient to actuate the second response button to indicate that the patient is conscious.

10. The system of claim 6, wherein the notification includes a warning message of imminent shock.

11. The system of claim 10, wherein the processor is configured to cause the audio output device to provide the notification immediately upon determining that the received communication is an urgent communication.

12. The system of claim 1, wherein the remote device further comprises an audio circuit configured to convert information included in the communication received from the wearable cardioverter defibrillator to an audio signal capable of being reproduced by the audio output device.

13. The system of claim 1, wherein the communication interface is configured to communicate with the wearable cardioverter defibrillator wirelessly.

14. The system of claim 1, wherein:
the remote device further comprises a visual touch screen display by which the patient can provide input to, and receive information from, the remote device; and
the second response button is a virtual button displayed on the visual touch screen display.

15. The system of claim 1, wherein:
the remote device further comprises a visual touch screen display by which the patient can provide input to, and receive information from, the remote device; and
the visual touch screen display is further configured to display the communication received from the wearable cardioverter defibrillator.

16. The system of claim 1, wherein:
the communication received from the wearable cardioverter defibrillator comprises a code;
the processor is further configured to determine a message by looking up the code in a message table that is stored in the memory; and
the processor is further configured to determine whether the received communication is an urgent communication based on the determined message.

17. The system of claim 1, wherein:
the remote device further comprises an electromechanical vibrator; and
the processor is configured to energize the electromechanical vibrator in response to determining that the received communication is an urgent communication.

18. The system of claim 17, wherein determining that the received communication is an urgent communication comprises determining that the received communication was generated in response to the wearable cardioverter defibrillator detecting the treatable cardiac condition.

19. The system of claim 1, wherein determining that the received communication is not an urgent communication comprises determining that the received communication corresponds to a detected arrhythmia that abated before any therapeutic shock was delivered to the patient.

20. The system of claim 1, wherein determining whether the received communication is an urgent communication at least partially depends on a time of day at which the communication was received by the remote device.

* * * * *